US012805755B2

(12) United States Patent
Mastrogiovanni et al.

(10) Patent No.: US 12,805,755 B2
(45) Date of Patent: Nov. 24, 2026

(54) APPARATUS FOR DETECTING AND TRACKING THE POSITION AND/OR DEFORMATION OF A BODY ORGAN

(71) Applicants: IOS HOLDING SUISSE SA, Lugano (CH); Marco Bressani, Genoa (IT)

(72) Inventors: Fulvio Mastrogiovanni, Genoa (IT); Carlo Terrone, Torina (IT); Paolo Traverso, Genoa (IT)

(73) Assignees: IOS HOLDING SUISSE SA, Genoa (IT); Marco Bressani, Lugano (CH)

( * ) Notice: Subject to any disclaimer, the term of this patent is extended or adjusted under 35 U.S.C. 154(b) by 613 days.

(21) Appl. No.: 18/003,221

(22) PCT Filed: May 3, 2021

(86) PCT No.: PCT/EP2021/061517

§ 371 (c)(1),
(2) Date: Dec. 23, 2022

(87) PCT Pub. No.: WO2021/259537

PCT Pub. Date: Dec. 30, 2021

(65) Prior Publication Data

US 2023/0248264 A1 Aug. 10, 2023

(30) Foreign Application Priority Data

Jun. 25, 2020 (IT) ........................ 102020000015322

(51) Int. Cl.
*A61B 5/11* (2006.01)
*A61B 34/10* (2016.01)
*A61B 90/00* (2016.01)

(52) U.S. Cl.
CPC ............ *A61B 5/1114* (2013.01); *A61B 34/10* (2016.02); *A61B 2034/105* (2016.02);
(Continued)

(58) Field of Classification Search
CPC ............ A61B 5/1114; A61B 2034/105; A61B 2090/365; A61B 2090/372; A61B 2562/0219
See application file for complete search history.

(56) References Cited

U.S. PATENT DOCUMENTS 9,392,960 B2 * 7/2016 Zvuloni ............. A61B 10/0241
10,413,364 B1 * 9/2019 Yu .................... A61B 1/000096
(Continued)

FOREIGN PATENT DOCUMENTS

WO 2012/006636 A1 1/2012
WO WO-2016005988 A1 * 1/2016 ......... A61B 1/00147
(Continued)

OTHER PUBLICATIONS

Wang et al., "Real Time 3d Visualization of Intraoperative Organ Deformations Using Structured Dictionary", IEEE Transations on Medical Imaging, IEEE Service Center, Piscataway, NJ, US, vol. 31, No. 4, (Apr. 1, 2012), pp. 924-937, XP011491076.
(Continued)

*Primary Examiner* — Alex M Valvis
(74) *Attorney, Agent, or Firm* — ASLAN LAW, P.C.

(57) ABSTRACT

A detection and tracking apparatus for detecting and tracking the position and/or deformation of a body organ subject to manipulation, comprising at least one processing unit, in communication with a receiving unit and with a wearable
(Continued)

and/or portable display device, performing the following steps: a) determining a representation of the position and/or deformation of the organ; b) associating a three-dimensional augmented reality image of the organ with the representation of the position and/or deformation thereof; c) overlaying the three-dimensional augmented reality image with the position and/or deformation of the organ through the display device; d) tracking the position and/or deformation image in correspondence with the position and/or deformation of the organ of which the three-dimensional augmented reality image is a representation, comparing the information about the position and/or deformation associated with that position and/or deformation with a plurality of predefined models of position and/or deformation of the position and/or deformation.

8 Claims, 1 Drawing Sheet

(52) U.S. Cl.
CPC ... *A61B 2090/365* (2016.02); *A61B 2090/372* (2016.02); *A61B 2505/05* (2013.01); *A61B 2562/0219* (2013.01)

(56) References Cited

U.S. PATENT DOCUMENTS

| | | | | |
|---|---|---|---|---|
| 2011/0046483 | A1* | 2/2011 | Fuchs | A61B 18/1477 606/20 |
| 2017/0042626 | A1* | 2/2017 | Egorov | A61B 34/10 |
| 2018/0249151 | A1* | 8/2018 | Freeman | G06V 20/20 |
| 2019/0117317 | A1* | 4/2019 | Abayazid | A61B 5/066 |
| 2019/0380792 | A1* | 12/2019 | Poltaretskyi | G06N 3/08 |
| 2020/0113542 | A1* | 4/2020 | Perrey | A61B 8/4254 |
| 2021/0141443 | A1* | 5/2021 | Fukumoto | G01B 21/00 |
| 2023/0320830 | A1* | 10/2023 | Lamraoui | A61F 5/48 600/424 |

FOREIGN PATENT DOCUMENTS

| | | | | |
|---|---|---|---|---|
| WO | 2017/151904 | A | 9/2017 | |
| WO | WO-2018148379 | A1 * | 8/2018 | G16H 30/40 |

OTHER PUBLICATIONS

International Search Report dated May 19, 2021, from corresponding application No. PCT/EP2021/061517.

* cited by examiner

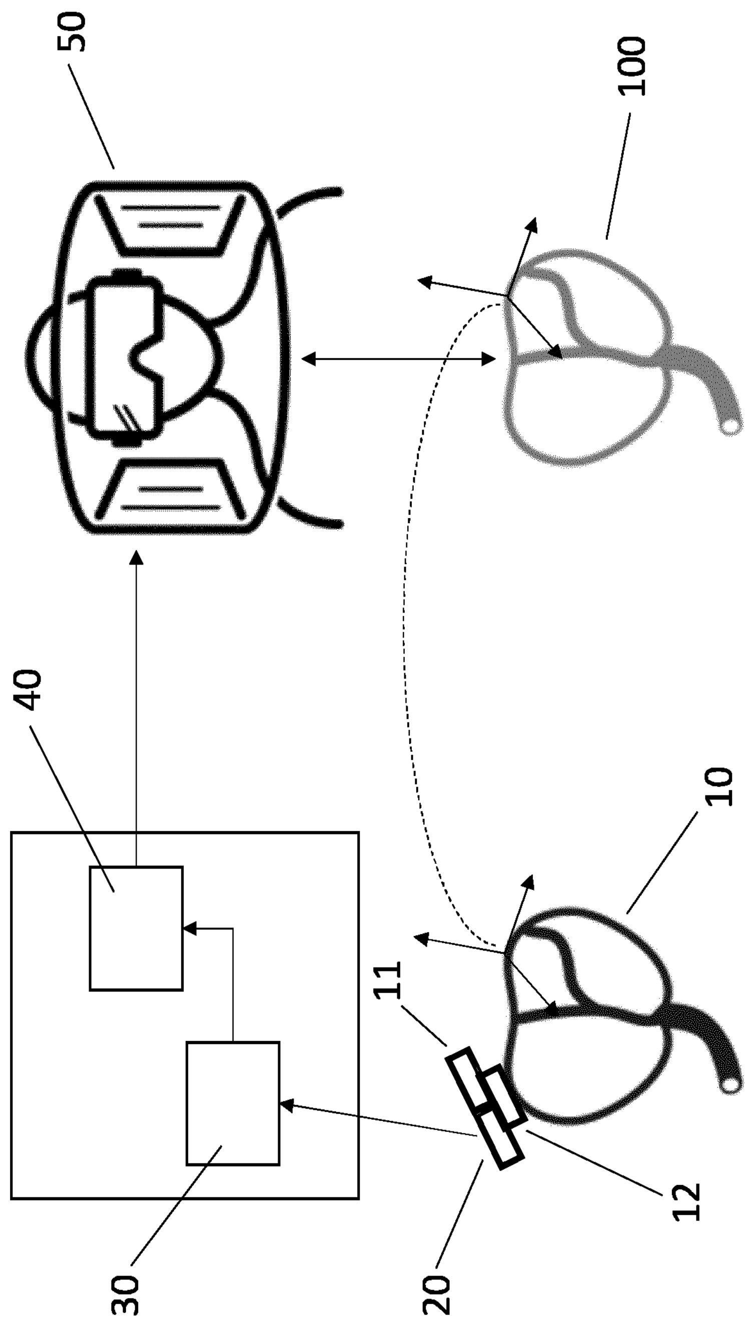
50
100
40
10
11
12
20
30

APPARATUS FOR DETECTING AND TRACKING THE POSITION AND/OR DEFORMATION OF A BODY ORGAN

CROSS REFERENCE TO RELATED APPLICATIONS

The present application is a U.S. National Phase Application under 35 U.S.C. § 371 of International PCT/EP2021/061517 filed May 3, 2021, which claims priority of Italian Patent Application No. 102020000015322 filed Jun. 25, 2020. The entire contents of which are hereby incorporated by reference.

FIELD OF THE INVENTION

The present invention relates to an apparatus and a method for detecting and tracking the position and deformation of a body organ in an intraoperative context, for example during surgical procedures.

BACKGROUND

The known systems presently being developed to achieve an assisted intracorporeal orientation aided by augmented reality techniques in the course of surgical procedures in an intraoperative context are based on a reconstruction of the three-dimensional augmented reality image of a body organ, which can be obtained using various techniques.

Based on the availability of such three-dimensional augmented reality images, there exist different known approaches that enable an association of the image with the organ to be obtained, and the tracking thereof in order to allow an assisted intracorporeal orientation in the course of surgical procedures in that intraoperative context.

Such traditional approaches can for example regard the superimposition of that image in the common space and manual tracking in the visual field of medical staff, for example a surgeon, by means of known augmented reality techniques.

Such approaches, and others based on similar technologies, are usable in an intraoperative context, for example during a surgical procedure, but they do not enable a valid, effective, certifiable real-time synchrony with the visual field of medical staff, for example a surgeon, by means of augmented reality techniques, both as regards an unsatisfactory precision in determining the position and/or deformation information and/or variations associated with that position and/or deformation of the organ, and as regards the reproduction thereof in the three-dimensional augmented reality image.

Possible systems known in the prior art that could be adopted for the purpose of detecting the position and/or deformation and/or variations associated with that position and/or deformation of an organ in a satisfactory manner, relate to body imaging techniques for diagnostic use, such as, for example, X-rays, computed tomography (CT), magnetic resonance imaging (MRI), and techniques based on similar principles.

These techniques are not utilizable in an intraoperative context, for example during a surgical operation, because their results are as a rule available offline, and can thus not be used to update the position and/or deformation related to the three-dimensional augmented reality image in correspondence with that position and/or deformation and/or variations associated with that position and/or deformation of the organ of which the augmented reality image is a representation.

Moreover, such techniques require equipment that is not compatible with an intraoperative context, especially in the course of a surgical operation.

At the current state of the art, the most common technologies that could be adopted in an intraoperative context, for example during a surgical operation, and which are not based on approaches related to body imaging for diagnostic use, are the following, or in any case they are based on similar principles:

- Cameras, or devices of a similar nature, arranged in the room and/or fixed in an appropriate and advantageous manner within the room near relevant equipment. Such cameras or devices of a similar nature can be used to frame the intraoperative context, for example during a surgical operation, and provide visual information from which to extract, by means of algorithms of an inductive or deductive type, characteristics useful for determining the position and/or deformation and/or variations associated with that position and/or deformation of the body organ.
- Motion capture systems, or devices of a similar nature, based on cameras and fiducial markers, in which the cameras are positioned in the room and/or fixed in an appropriate and advantageous manner within the room near relevant equipment, and in which the fiducial markers are mechanically fixed in an appropriate and advantageous manner to the body organ subject to the intraoperative context, for example during a surgical procedure.

Such motion capture systems, or devices of a similar nature, can be used to detect the position and/or the variations associated with the position of one or more fiducial markers mechanically coupled to the organ, and thus provide position information about the fiducial markers from which to extract, by means of algorithms of an inductive or deductive type, characteristics useful for determining the position and/or deformation and/or variations associated with that position and/or deformation of the body organ to which the fiducial markers are fixed.

- Location systems based on radio signals, such as, for example, the ones based on Wi-Fi technology or the like, in which at least one Wi-Fi signal emitter is positioned in the room and/or fixed in an appropriate and advantageous manner within the room near relevant equipment, and in which modulation data of that signal, such as, for example, amplitude and phase, can be considered information attributable, by means of algorithms of an inductive or deductive type, to characteristics useful for determining the position and/or deformation and/or variations associated with that position and/or deformation of the body organ. These technologies and those based on similar principles are often difficult to use in an intraoperative context, for example in the course of a surgical procedure, where camera-based systems might not frame the intraoperative context in an adequate manner and/or with the necessary precision, motion capture systems might not detect a sufficient number of fiducial markers mechanically coupled to the body organ in an adequate manner, and location systems based on radio signals might not be capable of isolating that organ in order to determine the position and/or deformation and/or variations associated with that position and/or deformation, and/or in any case in a sufficiently precise and reliable manner to determine a representation of the position and/or deformation of the organ in the course of that intraoperative context, especially during a surgical procedure.

These technologies and those based on similar principles often do not ensure satisfactory performances in terms of precision of the determination of the position and/or deformation and/or variations associated with that position and/or deformation of a body organ in an intraoperative context, for example during a surgical operation, a context that is not suitable for the determination of the position and/or deformation using, for example:

- information obtained from cameras, because of occlusions due to the particular configuration of the intraoperative context, such as, for example, the presence of objects, medical devices, medical staff or other body organs, which are interposed between the cameras and the body organ whose position and/or deformation it is desired to determine, or because of the non-appropriate resolution of that information for the purpose of determining that position and/or deformation, due to the distance at which the cameras must be placed in order not to negatively impact the intraoperative context, such as, for example, the need not to disturb the operations of medical staff, for example a surgeon, who is working there;
- information obtained from motion capture systems, because of occlusions due to the particular configuration of the intraoperative context, such as, for example, the presence of medical staff, objects, medical devices, or other body organs, which are interposed between the cameras and one or more fiducial markers mechanically coupled to the body organ whose position and/or deformation it is desired to determine, or because of the need to simultaneously detect a sufficient number of such fiducial markers in order to determine that position and/or deformation, due to positions often not suited to the purpose for which such fiducial markers can be placed on that organ so as not to negatively impact the intraoperative context, such as, for example, the need not to impede the freedom of the actions of medical staff, for example a surgeon, who is working there;
- information obtained from location systems based on radio signals, such as, for example, the ones based on Wi-Fi technology or the like, because of the inability of such signals to isolate and segment the body organ whose position and/or deformation it is desired to determine, or because of the inadequate precision with which such segmentation can be done, as a result of fluctuations of the modulations of the radio signals due to the environment in which the intraoperative context, for example a surgical procedure, arises.

A typical example of an unsuitable environment is represented by areas, zones, or rooms used for activities of a medical nature where various objects for medical use, various medical devices, and various members of the medical staff are present, such as, for example, operating rooms in which surgeons operate, or in general areas, zones, or rooms where an intraoperative context can arise.

Thus, there is a felt need to improve the known systems and methods for detecting and tracking the position and deformation of a body organ in an intraoperative context, for example in the course of surgical procedures.

SUMMARY

The technical task of the present invention is therefore to provide an apparatus and a method for detecting and tracking the position and deformation of a body organ in an intraoperative context, for example in the course of surgical procedures, which allows the aforementioned technical drawbacks of the prior art to be eliminated.

Within the scope of this technical task one object of the invention is to provide an apparatus for detecting and tracking the position and deformation of a body organ in an intraoperative context, for example during surgical procedures, which enables a three-dimensional augmented reality image of that organ to be associated with said representation of the position thereof and/or deformation thereof, in a simple, effective and safe manner.

Another object of the invention is to provide an apparatus for detecting and tracking the position and deformation of a body organ in an intraoperative context, for example in the course of surgical procedures, which enables the assisted intracorporeal orientation to be guided in the course of surgical procedures in the intraoperative context.

Yet a further object of the invention is to provide an apparatus for detecting and tracking the position and deformation of a body organ in an intraoperative context, for example during surgical procedures, which provides data of an absolute or time-differential type localized on the surface of that organ.

The technical task, as well as these and other objects according to the present invention, are achieved by providing a detection and tracking apparatus for detecting and tracking at least the position of a body organ subject to manipulation, characterized in that it has:

- at least one detection sensor for detecting the position of said body organ, configured to provide information of an absolute or time-differential type;
- a rigid coupling means for coupling said at least one detection sensor to said body organ;
- at least one transmitting unit for transmitting the information about said position of an absolute or time-differential type detected by said detection sensor;
- at least one receiving unit for receiving said information about said position of an absolute or time-differential type transmitted by said transmitting unit;
- at least one wearable and/or portable display device;
- at least one processing unit, in communication with said receiving unit and with said display device, configured to perform the following steps of a procedure for evaluating said information about said position of an absolute or time-differential type:
- a) determining a representation of said position of said organ, said processing unit having an inductive or deductive algorithm for determining said representation;
- b) associating a three-dimensional augmented reality image of said organ with said representation of said position thereof;
- c) overlaying said three-dimensional augmented reality image with the position of said organ in a common three-dimensional space through said wearable and/or portable display device;
- d) tracking said position of said three-dimensional augmented reality image in correspondence with the position of said organ of which said three-dimensional augmented reality image is a representation, comparing said information about said position with a plurality of predefined models of position of organs.

In one embodiment of the invention, when the body organ under manipulation is rigid or almost rigid like the prostate, one single detection sensor can be enough.

In an embodiment of the invention, at least when the organ is deformable, at least two detection sensors for detecting the position and deformation of said body organ are provided for; said at least one transmitting unit being configured to transmit the information about said position and said deformation of an absolute or time-differential type detected by said detection sensors; said at least one receiving unit being configured to receive said information about said position and said deformation of an absolute or time-differential type transmitted by said transmitting unit said at least one processing unit being configured to determine a representation of said position and said deformation of said organ, associate a three-dimensional augmented reality image of said organ with said representation of said position and said deformation thereof, overlaying said three-dimensional augmented reality image with the position and deformation of said organ in the common three-dimensional space through said wearable and/or portable display device; tracking said position and said deformation of said three-dimensional augmented reality image in correspondence with the position and deformation of said organ of which said three-dimensional augmented reality image is a representation, comparing said information about said position and said deformation with a plurality of predefined models of position and deformation of organs.

BRIEF DESCRIPTION OF THE DRAWINGS

Further features and advantages of the invention will become more apparent form the description of a preferred, but not exclusive, embodiment of the apparatus for detecting and tracking the position and/or deformation of a body organ, which is illustrated by way of approximate and non-limiting example in the attached drawing, of which:

FIG. 1 shows the tracking apparatus for detecting and tracking the position and/or deformation of a body organ subject to manipulation.

DETAILED DESCRIPTION

The body organ is selected among thoracic internal organs, abdominal organs and pelvic organs.

In more detail, the body organ in selected among organs of the cardiovascular system comprising large arterial and venous vessels and heart, organs of the respiratory system comprising lungs and airway and mediastinal structures, organs of the digestive system comprising liver, esophagus, stomach, Gallbladder, pancreas, intestine, rectum intestine, splanchnic organs comprising spleen, and organs of the urinary and reproductive system comprising kidney, ureters, bladder, prostate, uterus, ovaries, vagina.

Other features of the invention are defined in the subsequent claims.

Additional features and advantages of the invention will become more apparent from the description of a preferred but not exclusive embodiment of an apparatus for detecting and tracking the position and/or deformation of a body organ which is subject to manipulation in an intraoperative context, for example in the course of surgical procedures according to the invention, illustrated by way of non-limiting example in the accompanying drawings, in which:

in FIG. 1 the invention is schematized and exemplified. With reference to aforementioned Figure, it shows an apparatus for detecting and tracking the position and/or deformation of a body organ which is subject to manipulation in an intraoperative context, for example in the course of surgical procedures, denoted in its entirety by the reference number (1).

The body organ (10) has at least one detection sensor (11) for detecting the position and/or deformation, configured to provide information of an absolute or time-differential type, and a rigid coupling means (12) for coupling the at least one sensor to the organ.

The sensor (11) detects information about the position and/or deformation and a transmitting unit (20) transmits the information to a receiving unit (30).

A processing unit (40), in communication with the receiving unit (30) and with at least one wearable and portable display device (50), is configured to perform successive steps of a procedure for evaluating the information detected by the detection sensor (11).

Through algorithms and procedures of an inductive or deductive type, the processing unit (40) determines a representation of the position and/or deformation of the body organ (10) in the course of the intraoperative context.

Said representation of the position and/or deformation of the body organ (10) can be in form of spatial coordinates of a set of points and angles, for instance spatial coordinates of a set of three points and three angles.

Then the processing unit (40) associates a three-dimensional augmented reality image (100) of the organ (10) with the representation of the position thereof and/or deformation thereof, and overlays the three-dimensional augmented reality image (100) on the body organ (10) in the common three-dimensional space through the wearable and/or portable display device (50), typically through known augmented reality techniques.

The processing unit (40) then tracks the position and/or deformation of the three-dimensional augmented reality image (100) in correspondence with the position and/or deformation of the body organ (10) of which the augmented reality image (100) is a representation in the course of the intraoperative context, comparing the information about the position and/or deformation and/or variations associated therewith with a plurality of predefined models of position and/or deformation and/or evolution of that position and/or deformation.

In an advantageous configuration of the apparatus, said parameters and said predefined models can be rendered specific for different types of internal body organs through a calibration step, whereby, by means of algorithms and procedures of a deductive type, it is possible, for every such type of internal body organ, to determine a model for determining the position and/or deformation and/or variations associated with that position and/or deformation.

Similarly, through a learning step based on algorithms and procedures of an inductive type, it is possible, for every type of internal body organ, to generalize a model for determining the position and/or deformation and/or variations associated with that position and/or deformation, as a consequence of actions of manipulation in an intraoperative context, for example in the course of surgical procedures.

Such actions correspond to conditions of usual behavior in carrying out surgical procedures, there being available for this purpose an algorithm for predicting said position and/or deformation which is in the form of an inductive or deductive algorithm, such as, for example, a computational model based on a neural network or other approximation algorithms capable of carrying out learning cycles during the current use or procedures in a closed form.

By way of example, the inventors have been able to observe that, thanks to the use of algorithms of an inductive type, for example based on neural networks, it is possible to recognize and track the evolution of the position and/or deformation and/or variations associated with that position and/or deformation of an internal organ subject to an intraoperative context, such as, for example, a surgical procedure, by analyzing solely differential movement data of that organ in that context, without the need to use cameras, motion capture systems, or location systems based on radio signals, as in the known systems.

All this with a clear benefit for the construction of a system of assisted intracorporeal orientation that is reliable in the course of that surgical procedure in that intraoperative context, and also in terms of the precision of the surgical procedure and cost reduction.

As a further example, the inventors have been able to observe that, thanks to the use solely of differential movement data, it is possible to associate a three-dimensional augmented reality image of the organ with said representation of the position thereof and/or deformation thereof, and then overlay the three-dimensional augmented reality image with the position and/or deformation of said organ in the common three-dimensional space through a wearable or portable display device, and then update the position and/or deformation of the three-dimensional augmented reality image in correspondence with the position and/or deformation of the organ, for example by means of augmented reality technologies, for the purpose of improving the performance of the surgical procedure.

The operation of the apparatus for detecting and tracking the position and/or deformation of a body organ subject to manipulation in an intraoperative context (1) according to the invention appears clear from what is described and illustrated and, in particular in a first preferred but not exclusive embodiment, it is substantially the following.

A three-dimensional scan of the body organ (10) is considered to be available, of which we define a particular instance as 0, subjected to a surgical operation, to be used as a augmented reality image (100), of which we define a particular instance as I.

I is to be considered as a set RI of M elements, such that RI=(Q_1, . . . , Q_i, . . . , Q_M), where the generic element Q_i is a set of three values (x_i, y_i, z_i) which represents the position of Q_i in the common space with respect to a Cartesian reference system W, appropriately defined.

A display device (50) is considered to be available, of which we define a particular instance as a see-through display for augmented reality now identified as H, such as, for example, a commercial Microsoft Hololens or similar device or a 3D robotic visor.

N detection sensors (11) are considered to be available, typically inertial sensors, such as, for example, accelerometers, gyroscopes, magnetometers, devices identified as a particular instance of a set D_1, . . . , D_i, . . . , D_N, from which data can be acquired either via a cable or by means of a wireless connection.

The devices D_1, . . . , D_i, . . . , D_N can be secured to the organ O by means of a coupling means (12), typically a mechanical fastening.

A surgical robot R, not necessarily provided with haptic feedback, is considered to be available; it is not illustrated in the Figures.

It is thus considered that the organ O can be reached by the surgeon C, and that access to the operating site and the related procedures of positioning the operating instruments have been completed.

The operation of the apparatus for detecting and tracking the position and/or deformation of a body organ subject to manipulation in an intraoperative context 1 according to the invention comprises the following steps.

Step 1

The devices D_1, . . . , D_i, . . . , D_N are initially arranged in a predefined position in order to be calibrated, i.e. so as to register the respective Cartesian reference systems with respect to the Cartesian reference system W.

Consequently, the transformations between a generic device D_i and the reference system W, and between W and the various D_1, . . . , D_i, . . . , D_N are known.

Step 2

The position of the display H is calibrated, i.e. the relevant Cartesian reference system, and this also means the one associated with the augmented reality space managed by H, is registered with respect to the Cartesian reference system W. Consequently, the transformations between H and W, and between W and H, and consequently the transformations between the devices D_1, . . . , D_i, . . . , D_N and H, and between H and the various devices D_1, . . . , D_i, . . . , D_N are known.

Step 3

The devices D_1, . . . , D_i, . . . , D_N are introduced into the abdomen and fixed to the surface of the organ O by the surgeon C, in such a way as to:

(i) prioritize the zones on the surface of O where he or she expects the maximum deformation induced by mechanical and manipulation stresses, and (ii) if the acquisition of data by the devices D_1, . . . , D_i, . . . , D_N is via cable, maximize the probability that the cables will not obstruct the work of the surgeon C and in particular do not interfere with working space of the robot R.

Step 4

The devices D_1, . . . , D_i, . . . , D_N are powered, and then every device D i generates a time series S_i at a certain frequency F_i.

The symbol S_i can also be understood as a reference to the specific inertial sensor of the associated device D i.

It is realistically assumed that the frequencies are all equal, i.e. F_1= . . . =F_N, and thus that said frequencies can be referred to overall as F.

Every time series S_i is composed at every instant t of a pair (A_t, V_t), where A t indicates the linear acceleration vector and consists of a set of three (a_x, a_y, a_z), wherein a_x is the linear acceleration along the x axis, a_y is the linear acceleration along the y axis, a_z is the linear acceleration along the z axis (said axes are to be understood as with respect to the reference system of the device D_i, but transformable into the respective values with respect to the Cartesian reference system W), and V t indicates the angular velocity vector and consists of a set of three (v_x, v_y, v_z), wherein v_x is the angular velocity around the x axis, a_y is the angular velocity around they axis, a_z is the angular velocity around the z axis (in this case as well, said axes are understood as with respect to the reference system of the device D_i, but transformable into the respective values with respect to the Cartesian reference system W).

S_it=(A_it, V_it) refers to the pair related to the time series S_i at the time instant t, for every i comprised between 1 and N and for every t between 1 and T, corresponding to the duration of the surgical procedure.

Step 5

For every device D_i and instant t, S_it is acquired by the sensor S_i, is transmitted by a transmitting unit (20), of which we now consider a specific instance defined as TX_i, is received by a receiving unit (30), of which we now consider a specific instance defined as RX, which concentrates the signals coming from all of the devices, and is then provided to an algorithm ALG_P which is run on a processing unit (40), of which we now consider a specific instance defined as a computing device E. This takes place at a frequency F.

Step 6

When the display H is worn by the surgeon C, the latter sees two superimposed representations of the world, the augmented space SA (generated artificially by H) and the common space SC.

In relation to the representation SA, the surgeon C sees the image I of the organ 0 floating in space and in a certain position PI.

Reference is made to that position in a certain instant t as PI_t, for every t comprised between 1 and T, corresponding to the duration of the surgical procedure.

At every instant t, PI_t is the result of the operations of the algorithm ALG_P, the behavior of which is subsequently described in STEP_9.

In relation to the representation SC, the surgeon C sees the intraoperative context in which the position of 0, to which we refer as PO, does not correspond to that of PI.

Step 7

Subsequently, the two positions PI and PO must be registered with respect to the reference system W.

This is done in an automatic mode.

An algorithm ALG_R implements a known technique of three-dimensional visual servoing.

ALG_R has as input the image I and the sensorial proximity data provided by H, conveniently represented as a vector RH of U elements such that RH=(Q_1, . . . , Q_i, . . . , Q_U), where every element Q_i is a set of three values (x_i, y_i, z_i) that represents the position, in the augmented space SA, of Q_i, with respect to the reference system of H, but it can obviously refer to W.

ALG_R has the purpose of superimposing I on 0, and m particular of superimposing the two respective positions PI and PO.

ALG_R considers the subset RO of the vector RH, which contains the points Q_i in RH corresponding to the organ 0, and implements a technique of minimizing a cost function that depends on a distance metric between RI and RH in the augmented space SA, or a learning-based technique that determines an equivalent metric, or a technique based on multi-physical simulation.

The distance metric can advantageously be deterministic or probabilistic.

In the former case, when the value of the cost function is lower than a certain threshold SQ_1, it means that the image I and the organ O are superimposed, and in particular that the two positions PI and PO, respectively of the image and of the organ, are superimposed.

In the latter case, when the value of the cost function and of the main moments thereof are characterized by certain statistical properties defined as a whole as SQ_1, it means that the image I and the organ O are superimposed, and in particular that the two positions PI and PO, respectively of the image and of the organ, are superimposed.

Step 8

The surgeon C, during the operating step, manipulates the organ O by acting on the R robot, and consequently the organ O is moved.

From an operational viewpoint, it is advantageous to consider the organ O as a rigid body. This implies that PI (respectively, PO) is a vector of values (p_x, p_y, p_z, o_x, o_y, o_z), where p_x is the position of I (respectively, 0) relative to the x axis, p_y is the position of I (respectively, 0) relative to the y axis, p_z is the position of I (respectively, 0) relative to the z axis, o_x is the orientation of I (respectively, 0) relative to the x axis, o_y is the orientation of I (respectively, 0) relative to the y axis, o_z is the orientation of I (respectively, 0) relative to the z axis, all with respect to the Cartesian reference system W.

Step 9

While the organ O is moved following the actions of the surgeon C, for every instant t, with t comprised between 1 and T, N data in the form of S_it=(A_it, V_it), one for every device D_i, are processed by ALG_P.

ALG_P implements a nonlinear probabilistic estimation algorithm, which can be obtained through learning models or be in a closed form; it generates the estimated values of the variables of PI_t using a model that integrates the values of A_it twice and the values of V_t once, thereby determining the position of the image I within the space SA registered with respect to the Cartesian reference system W.

Step 10

At every instant t, with t comprised between 1 and T, PI_t is used to update the position of the image I, and consequently the form of the vector RI within the space SA registered with respect to the Cartesian reference system W, as viewed by the surgeon C.

Step 11

As the surgeon C acts on the organ 0, the various devices D_1, . . . , D_i, . . . , D_N, and for every instant of time t comprised between 1 and T, generate time series S_it which, processed by ALG_P, contribute to the calculation of the position PI_t of the image I and thus to the tracking of the position PO_t of the organ O through the estimation of the position PI_t. From a technological viewpoint, the objective is to minimize, for every t comprised between 1 and T, a deterministic or probabilistic distance metric between PI_t and PO_t (which corresponds to the distance metric between RI and RH in the augmented space SA), and in any case to ensure that this is contained within (or is compatible with) the threshold SQ_1.

Step 12

When the surgical procedure is completed, that is, when t is equal to T, the devices D_1, . . . , D_i, . . . , D_N are removed from the surface of 0.

A second preferred embodiment provides for an extension EXT-STEP 8 of STEP_8 described above, as follows.

The surgeon C, during the operating step, manipulates the organ O by acting on the robot R, and consequently the latter 1*s* deformed as a result of the surgical procedure.

From an operational viewpoint, it is now possible to consider the organ O as a deformable body.

It is assumed that the various devices D_1, . . . , D_i, . . . , D_N are positioned on the surface of O and that the various time series S_it=(A_it, V_it), with t comprised between 1 and T, represent the movements of the surface zones in which the various devices have been secured to 0.

It is further assumed that a characterization of the main mechanical characteristics of the organ O is available, for example in the form of stress-strain relations, or that there exists a model of such relations in multi-physical simulation, or in any case that said model can be obtained through learning techniques.

This implies that PI (respectively, PO) is a vector composed of N elements, each of the which in the form (p_x, p_y, p_z, o_x, o_y, o_z)_i, with i comprised between 1 and N, where p_x i-th is the position of D_i relative to the x axis, p_y i-th is the position of D_i relative to the y axis, p_z i-th is the position of D_i relative to the z axis, o_x i-th is the orientation of D_i relative to the x axis, o_y i-th is the orientation of D_i relative to the y axis and o_z i-th is the orientation of D_i relative to the z axis, all with respect to the Cartesian reference system W.

By means of known optimization algorithms, it is possible to calculate or estimate the deformation of the image I of the organ O at the instant t DE_t on the basis of PI_t and the stress-strain relation of 0, and consequently to determine I on the basis of PI_t and DE_t.

A third preferred embodiment comprises an alternative ALT-STEP_7 to STEP_7 as described above, as follows.

Following STEP_6, the two positions PI and PO must be registered with respect to the Cartesian reference system W.

This is done in an assisted mode by the surgeon C.

To begin with, an algorithm ALG_RA executes the algorithm ALG_R, which implements a known three-dimensional visual serving technique.

ALG_R has as input the image I and the sensorial proximity data provided by the device H, conveniently represented as a vector RH of U elements such that RH=(Q_1, . . . , Q_i, . . . , Q_U), where every element Q_i is a set of three values (x_i, y_i, z_i) that represents the position in the augmented space SA of Q_i, with respect to the reference system of H, but it can refer to W.

ALG_R has the purpose of superimposing I on 0, and m particular of superimposing the two positions PI and PO.

ALG_R considers the subset RO of the vector RH, which contains the points Q_i in RH corresponding to the organ 0, and implements a technique of minimizing a cost function that depends on a distance metric between RI and RH in the augmented space SA, or a learning-based technique that determines an equivalent metric, or a technique based on multi-physical simulation.

The distance metric can advantageously be deterministic or probabilistic.

In the former case, when the value of the cost function is lower than a certain threshold SQ_1, it means that the image I and the organ O are superimposed, and in particular that the two positions PI and PO, respectively of the image and of the organ, are superimposed.

In the latter case, when the value of the cost function and of the main moments thereof are characterized by certain statistical properties defined as a whole as SQ_1, it means that the image I and the organ O are superimposed, and in particular that the two positions PI and PO, respectively of the image and of the organ, are superimposed.

In the event that the value of the cost function does not become lower than the threshold SQ_1 in the deterministic case, or the statistical properties of the value of the objective function are not compatible with those defined as SQ_1 in the probabilistic case within a certain time threshold SQ_2, the surgeon C is called on to make manual adjustments to PI, and then ALG_R resumes, starting from the data I associated with the PI obtained manually by the surgeon C.

These iterations are repeated in ALG_RA until the value of the cost function becomes lower than the threshold SQ_1 in the deterministic case, or the statistical properties become compatible with those of SQ_1, and it thus means that I and 0 are superimposed, and in particular that PI and PO are superimposed.

The manual adjustment can be made by the surgeon C in two steps:

(i) using a discrete movement by means of the interface of the device H, the surgeon C selects I, and (ii) making a continuous movement, he or she carries out a rotation-translation of I in such a way as to superimpose I on O to the best of his or her ability.

It has in practice been observed that an apparatus for detecting and tracking the position and/or deformation of a body organ subject to manipulation in an intraoperative context, for example subject to surgical procedures according to the invention, is particularly advantageous for associating a three-dimensional augmented reality image of that organ with said representation of the position thereof and/or deformation thereof, in a simple, effective and safe manner.

Another advantage of the invention is to provide an apparatus for detecting and tracking the position and deformation of a body organ in an intraoperative context, for example during surgical procedures, which enables assisted intracorporeal orientation to be achieved in the course of surgical procedures in the intraoperative context by overlaying a three-dimensional augmented reality image with the position and/or deformation of the body organ in the common three-dimensional space through a wearable or portable display device with a valid, effective and certifiable real-time synchrony with the visual field of medical staff.

Another advantage of the invention is that of providing an apparatus for detecting and tracking the position and/or deformation of a body organ in an intraoperative context, for example in the course of surgical procedures, which updates the position and/or deformation of the three-dimensional augmented reality image in correspondence with the position and/or deformation of the body organ, and of providing data of an absolute or time-differential type and localized on the surface of that organ.

An apparatus for detecting and tracking the position and/or deformation of a body organ subject to manipulation in an intraoperative context, for example subject a surgical procedures, thus conceived is susceptible of numerous modifications and variants, all falling within the scope of the inventive concept, as defined by the claims.

In practice, the materials and the devices used, as well as the dimensions, parameters and algorithms, can be any whatsoever according to needs and the state of science and technology.

The invention claimed is:

1. A detection and tracking apparatus for detecting and tracing at least a first position and a deformation of a body organ subject to manipulation, said body organ being selected among thoracic internal organs, abdominal organs and pelvic organs, comprising:

at least two detection sensors detecting said first position and said deformation of said body organ, configured to provide information about said first position and said deformation of an absolute or time-differential type;

a rigid coupling configured to couple each of said at least two detection sensors to said body organ;

a transmitting unit transmitting the information about said first position and said deformation of an absolute or time-differential type detected by said at least two detection sensors;

a receiving unit receiving said information about said first position and said deformation of an absolute or time-differential type transmitted by said transmitting unit;

a display device comprising at least one a wearable or portable feature;

a processing unit, in communication with said receiving unit and with said display device, configured to perform the following steps of a procedure for evaluating said information about said first position and said deformation of an absolute or time-differential type:

a) determining a representation of said first position and said deformation of said body organ, said processing unit comprising an inductive or deductive algorithm determining said representation;

b) associating a three-dimensional augmented reality image of said body organ with said representation of said first position and said deformation thereof;

c) overlaying said three-dimensional augmented reality image with the first position and said deformation of said body organ in a common three-dimensional space through said display device;

d) tracking said first position and said deformation of said three-dimensional augmented reality image in correspondence with the first position and said deformation of said body organ of which said three-dimensional augmented reality image is a representation, and e) comparing said information about said first position and said deformation with a plurality of predefined models of position and deformation of organs, wherein a result of said comparison is used to update a specific augmented reality visualization from a plurality of available visualizations to be displayed on the display device.

2. The detection and tracking apparatus according to claim 1, wherein at least one of said at least two detection sensors is an inertial sensor.

3. The detection and tracking apparatus according to claim 1, wherein said display device is a see-through augmented reality display.

4. The detection and tracking apparatus according to claim 1, wherein said inductive or deductive algorithm determining said representation comprises a nonlinear probabilistic estimation algorithm for estimating the position and/or said deformation of said body organ which generates estimated values using a model that integrates acceleration values two times and velocity values one time.

5. The detection and tracking apparatus according to claim 4, wherein said estimation algorithm is obtained by learning models.

6. The detection and tracking apparatus according to claim 4, wherein said estimation algorithm is in a closed form.

7. The detection and tracking apparatus according to claim 1, wherein said at least two detection sensors comprises an accelerometer or a gyroscope or magnetometer configured for the transmission of data via a cable or by means of a wireless connection.

8. The apparatus of claim 1, wherein said processing unit is further configured to perform a learning step based on algorithms and procedures of an inductive type whereby, for every type of body organ, a corresponding model for determining said position and/or said deformation is generalized.

* * * * *